US006456880B1

(12) United States Patent
Park et al.

(10) Patent No.: US 6,456,880 B1
(45) Date of Patent: Sep. 24, 2002

(54) IMPLANTABLE CARDIAC STIMULATION DEVICE FOR AND METHOD OF MONITORING PROGRESSION OR REGRESSION OF A PATIENT'S HEART CONDITION BY MONITORING VENTRICULAR REPOLARIZATION INTERVAL DISPERSION

(75) Inventors: Euljoon Park, Stevenson Ranch, CA (US); Joseph J. Florio, La Canada, CA (US); Kerry Bradley, Glendale, CA (US); Gene A. Bornzin, Simi Valley, CA (US); Laurence S. Sloman, West Hollywood, CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 09/712,861

(22) Filed: Nov. 14, 2000

Related U.S. Application Data

(60) Provisional application No. 60/200,855, filed on May 1, 2000.

(51) Int. Cl.[7] .................................................. A61N 1/365
(52) U.S. Cl. .................................................. 607/25
(58) Field of Search ....................... 607/9, 25; 600/509, 600/510, 516

(56) References Cited

U.S. PATENT DOCUMENTS 5,306,293 A    4/1994  Zacouto ....................... 607/17
5,466,254 A   11/1995  Helland ....................... 607/123
5,560,368 A   10/1996  Berger ........................ 128/703
5,842,997 A   12/1998  Verrier et al. ............... 600/518
5,921,940 A    7/1999  Verrier et al. ............... 600/518
6,161,041 A *  12/2000  Stoop et al.

OTHER PUBLICATIONS

McLaughlin, Neil B., et al., "Comparison of Automatic QT Measurement Techniques in the Normal 12 Lead Electrocardiogram", British Heart Foundation, vol. 74, pp. 84–89, 1995.

Kautzner, Josef, et al., "QT Interval Dispersion and its Clinical Utility", PACE, vol. 20, Part II, pp. 2625–2640, Oct. 1997.

* cited by examiner

Primary Examiner—Scott M. Getzow

(57) ABSTRACT

An implantable cardiac stimulation device includes a system that monitors progression or regression of a patient's heart condition. The system includes a plurality of electrode configurations for sensing cardiac activity of the heart. A sensing circuit provides an electrical signal representing electrical activity of the heart from each of the sensing electrode configurations. A processor coupled to the sensing circuit determines, at spaced apart times, and over time, a ventricular repolarization interval in each of the electrical signals and a corresponding ventricular repolarization interval dispersion. A memory stores the ventricular repolarization interval dispersions for transmission by a telemetry circuit to an external receiver for analysis.

39 Claims, 4 Drawing Sheets

IMPLANTABLE CARDIAC STIMULATION DEVICE FOR AND METHOD OF MONITORING PROGRESSION OR REGRESSION OF A PATIENT'S HEART CONDITION BY MONITORING VENTRICULAR REPOLARIZATION INTERVAL DISPERSION

This application claims the benefit of U.S. Provisional Application No. 60/200,855, filed May 1, 2000.

FIELD OF THE INVENTION

The present invention is generally directed to an implantable device for monitoring the progression or regression of a patient's heart condition. The present invention is more particularly directed to a system and method for use in an implantable cardiac stimulation device which determines and stores ventricular repolarization interval dispersions over time. Relative changes in the ventricular repolarization interval dispersions, over time, are indicative of the progression or regression of the patient's heart condition.

BACKGROUND OF THE INVENTION

More people die of heart disease than any other single cause. Common forms of heart disease include congestive heart failure and malignant ventricular arrhythmias.

Congestive heart failure (CHF) is a debilitating, end-stage disease in which abnormal function of the heart leads to inadequate blood flow to fulfill the needs of the body's tissues. When the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the hardwalls to hamper rather than assist in providing cardiac output.

In patients with heart failure and malignant ventricular arrhythmias, the heart has often remodeled such that there is increased fibrosis between myocardial cells, a lengthening of the cells, varying degrees of hypertrophy and dilation, and up and down regulation of various receptors that effect ionic balance, action potential conduction, and contraction. These variations in the myocardial substrates often result in conduction abnormalities that increase the risk of arrhythmia.

Most cardiac patients with these heart conditions have an implanted cardiac stimulation device to administer therapy. It would therefore be most advantageous if the implanted devices were able to monitor the progression or regression of these heart conditions.

It has been observed that the ventricular repolarization duration of the hearts of these patients is spatially variable. Typically, this is measured with a standard 12 lead ECG by measuring the ventricular repolarization intervals with various lead combinations and subtracting the maximum ventricular repolarization interval from the minimum ventricular repolarization interval to derive a corresponding ventricular repolarization interval dispersion. Unfortunately, this procedure has not been practical in an implanted device because the implanted lead systems have been limited to the right side of the heart for sensing only local heart activity.

Implantable cardiac stimulation devices offering multi-chamber pacing (bi-ventricular or bi-atrial) and/or with defibrillation therapy offer an increased number of cardiac sensing electrode configurations including sensing configurations from the left side of the heart. The present invention provides a system and method for use in a multi-chamber implantable cardiac stimulation device which utilizes right and left heart sensing to advantage for measuring, over time, ventricular repolarization interval dispersion. This enables the implanted device to track the progression or regression of the patient's heart condition to effectuate more effective therapy titration.

SUMMARY OF THE INVENTION

The present invention provides a system and method for use in an implantable cardiac stimulation device for monitoring progression or regression of a patient's heart condition. In accordance with the present invention, the patient's heart condition is monitored by determining a ventricular repolarization interval dispersions spaced apart over time. Relative changes in the interval dispersion changes over time are indicative of the progression or regression in the patient's heart condition.

The ventricular repolarization interval dispersions are determined based upon the difference between a maximum ventricular repolarization interval measured with one of a plurality of electrode configurations and a minimum ventricular repolarization interval measured with another one of the plurality of electrode configurations.

The ventricular repolarization intervals may be QT intervals or alternatively, intervals beginning with a pacing stimulus and ending at the end of an immediately succeeding T-wave (Stim-T) interval. The plurality of electrode configurations may include right and left heart sensing electrode configurations to avoid localized sensing. Alternatively, two predetermined electrode configurations may be used to calculate the ventricular repolarization interval dispersion.

At each of the spaced apart times, a ventricular repolarization interval is determined for each electrode configuration. The interval dispersion is then determined from the maximum measured ventricular repolarization interval and the minimum measured ventricular repolarization interval and stored in a memory for later transmission to an external receiver by a telemetry circuit for analysis.

Pacing parameters by which the patient's heart may be adjusted responsive to the ventricular repolarization interval dispersions. For example, if the interval dispersions show an increasing trend, an interventricular delay may be modified to change the activation sequence such that the dispersions are reduced or, if the dispersions show a decreasing trend, the pacing rate may be reduced or the AV delay may be increased to allow increased intrinsic activity of the patient's heart.

The interval dispersions may be stored and conveyed with other parameters such as date and time of interval dispersion measurement, the heart rate, the individual ventricular repolarization intervals, and the patient's activity level. Still further, the times for determining the ventricular repolarization interval dispersions may be set to occur when the patient is normally at rest or may be conditioned upon the patient's heart rate or activity level being below predetermined limits. By controlling when this measurement occurs, accurate trending of the ventricular repolarization interval dispersions is facilitated.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
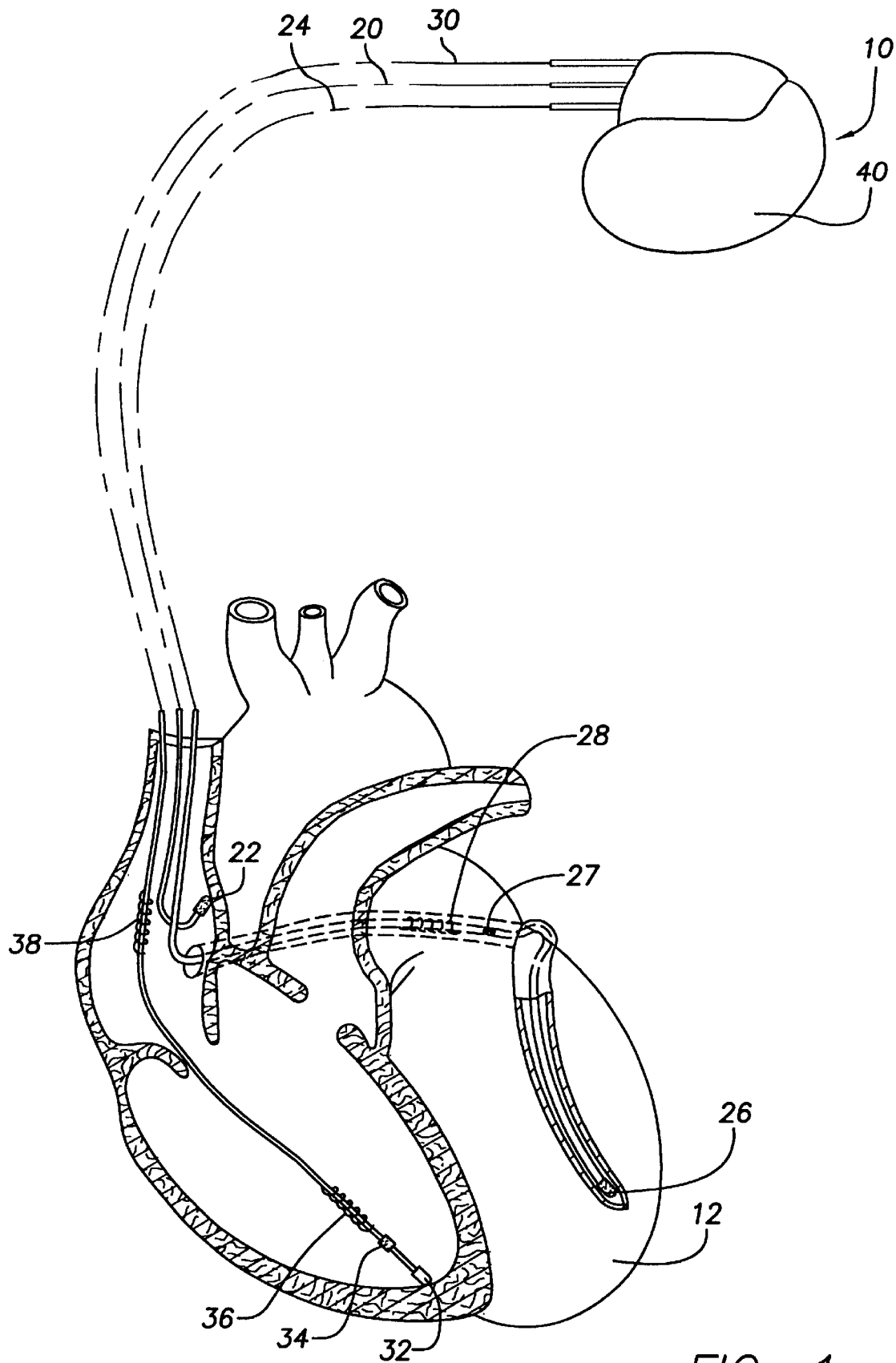
FIG. 1 is a simplified diagram illustrating an implantable stimulation device including a lead system providing a plurality of sensing electrode configurations in accordance with a preferred embodiment of the present invention and for delivering multi-chamber stimulation and shock therapy to a heart.

As shown in FIG. 1, there is a stimulation device 10 in electrical communication with a patient's heart 12 by way of three leads, 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place at least one electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead," which is a continuation-in-part of application Ser. No. 09/196,898, "A Self-Anchoring Coronary Sinus Lead" (Pianca et al.) (now abandoned); and U.S. Pat. No. 5,466,254, "Coronary Sinus Lead with Atrial Sensing Capability" (Helland), which patent application and patent, respectively, are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
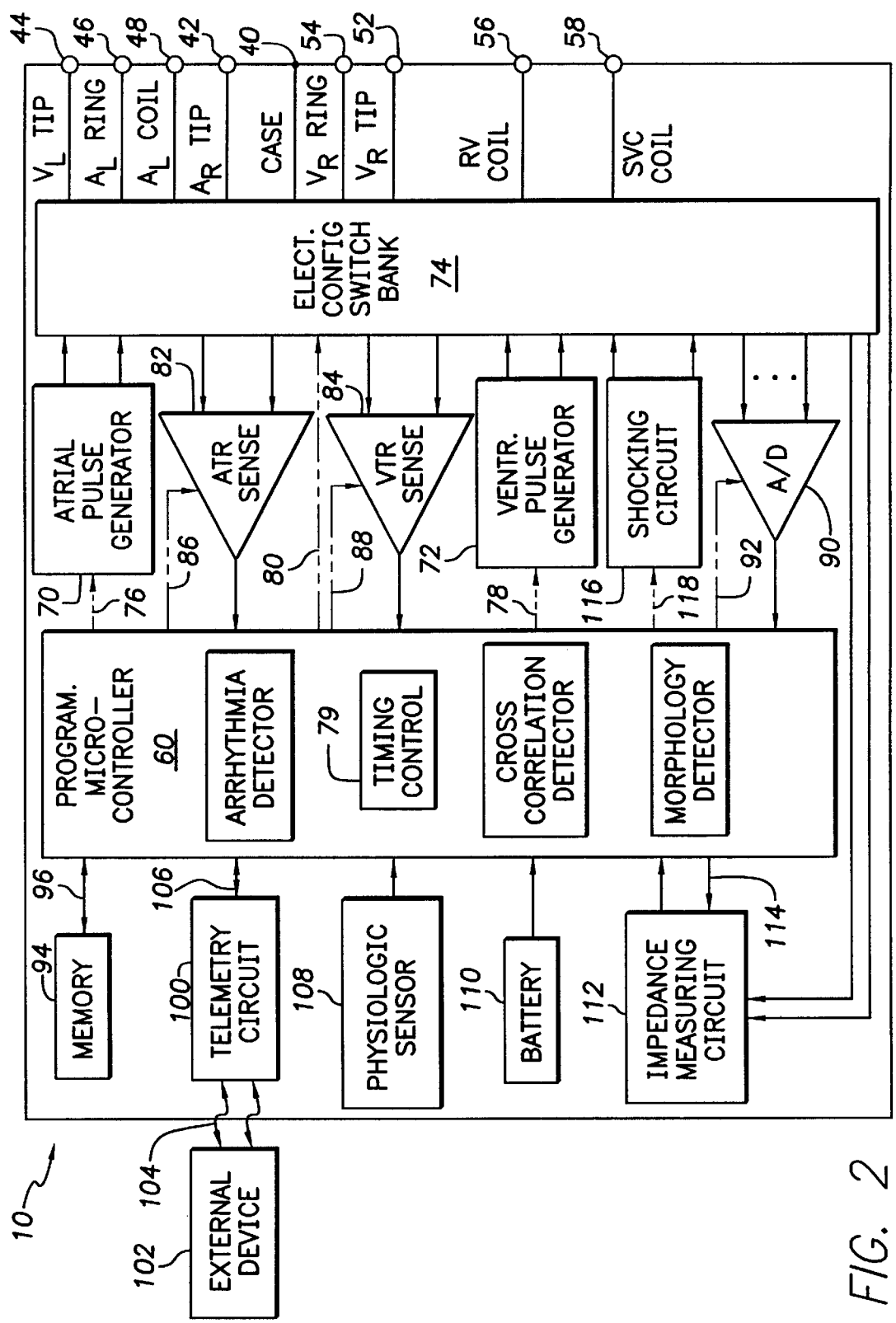
FIG. 2 is a functional block diagram of a multi-chamber implantable stimulation device embodying the present invention and illustrating the basic elements of a stimulation device which can provide cardioversion, defibrillation, and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown in FIG. 1 and schematically in FIG. 2, is often referred to as the "can", "case" or "case electrode" and may be programmably selected to act as the return electrode for all "unipolar" modes. The housing 40 may further be used as a return electrode alone or in combination with one of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial tip electrode 22.

To achieve left chamber sensing, pacing and shocking, the connector includes at least a left ventricular tip terminal 44, a left atrial ring terminal 46, and a left atrial shocking terminal 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal 52, a right ventricular ring terminal 54, a right ventricular shocking terminal 56, and an SVC shocking terminal 58, which are adapted for connection to the right ventricular tip electrode 32, right ventricular ring electrode, 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry or processor, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing circuitry which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74 for detecting the presence of cardiac activity in each of the four chambers of the heart. Accordingly, the atrial and ventricular sensing circuits, 82 and 84, may include dedicated sense amplifiers, multiplexed amplifiers, or shared amplifiers. The switch bank 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity, respectively, in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

In accordance with this preferred embodiment, the switch bank 74 is configured to select the plurality of sensing electrode configurations for measuring the ventricular repolarization intervals. The plurality of electrode configurations selected include electrodes positioned in both the right and left side of the heart to preclude localized sensing. To that end, the selected sensing electrode configurations may be for sensing between the right ventricular tip electrode 32 and the right atrial tip electrode 22, the right ventricular tip electrode 32 and the left ventricular tip electrode 26, the right ventricular tip electrode 32 and the case 40, the left ventricular tip electrode 26 and the case 40, the SVC coil electrode 38 and the left ventricular tip electrode 26, the left atrial ring electrode 27 and left ventricular tip electrode 26, the right ventricular ring electrode 34 and the case 40, a left ventricular ring electrode (not shown) and the case 40, and the right ventricular ring electrode 34 and the left ventricular ring electrode. The plurality of IEGM signals thus produced may be multiplexed by the data acquisition system 90, digitized and then stored in the memory 94 for use by the microcontroller 60 in determining a ventricular repolarization interval for each acquired signal. The ventricular repolarization interval dispersion is then determined by the microcontroller 60 by subtracting the minimum ventricular repolarization interval from the maximum ventricular repolarization interval. The microcontroller 60 may further derive and store for later transmission with the corresponding interval dispersion the date and time, the heart rate, and the patient's activity level. All of the foregoing, including each of the IEGM's is thereby made available for analysis with each determine ventricular repolarization interval dispersion.

The ventricular repolarization intervals may be traditional QT intervals or Stim-T intervals beginning with a pacing stimulation pulse, either single chamber or multi-chamber, and ending with the end of the next succeeding T-wave. The ventricular repolarization intervals, and hence the ventricular repolarization interval dispersions, are preferably measured periodically over time and when the patient is normally at rest. Further, the measurements may be conditioned on the patient's heart rate and/or activity level being below predetermined limits.

The microcontroller 60 is coupled to the memory 94 by a suitable data/address bus 96, where, in addition to the ventricular repolarization interval data, the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. In accordance with this embodiment of the present invention, after a ventricular repolarization interval dispersion is determined from the data acquired by the acquisition system 90, the trends of the interval dispersions are used by the microcontroller 60 in adjusting the programming of the device towards enhanced therapy.

The operating parameters of the implantable device 10 may be initially and non-invasively programmed into the memory 94 through a telemetry circuit 100 in telemetric communication with an external device 102, such as a programmer, transtelephonic transceiver, or a diagnostic system analyzer. The telemetry circuit 100 is activated by the microcontroller 60 by a control signal 106. The telemetry circuit 100 also allows the intracardiac electrograms, the ventricular repolarization interval data and interval dispersion results and status information relating to the operation of the device 10 (as contained in the microcontroller 60 or memory 94) to be sent to the external device 102 through the established communication link 104 for analysis.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, pacing mode, etc.) at which the atrial and ventricular pulse generators, 70 and 72, generate stimulation pulses. As previously mentioned, the sensor may further be used to determine the restful condition of the patient as a condition to measuring a ventricular repolarization interval dispersion. The sensor 108 may be, for example, an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

The stimulation device additionally includes a battery 110 which provides operating power to all of the circuits shown in FIG. 2. For the stimulation device 10, which employs shocking therapy, the battery must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries, as is currently true for most (if not all) such devices.

The stimulation device 10 further includes magnet detection circuitry (not shown), coupled to the microcontroller 60.

It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 by a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 120 is advantageously coupled to the switch bank 74 so that any desired electrode may be used. The impedance measuring circuit 112 is not critical to the present invention and is shown for only completeness.

It is the primary function of the device 10 to function as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11–40 joules), as controlled by the microcontroller 60. Such shocking pulses are applied to the patient's heart through at least two shocking electrodes, as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (e.g., using the RV electrode as common).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
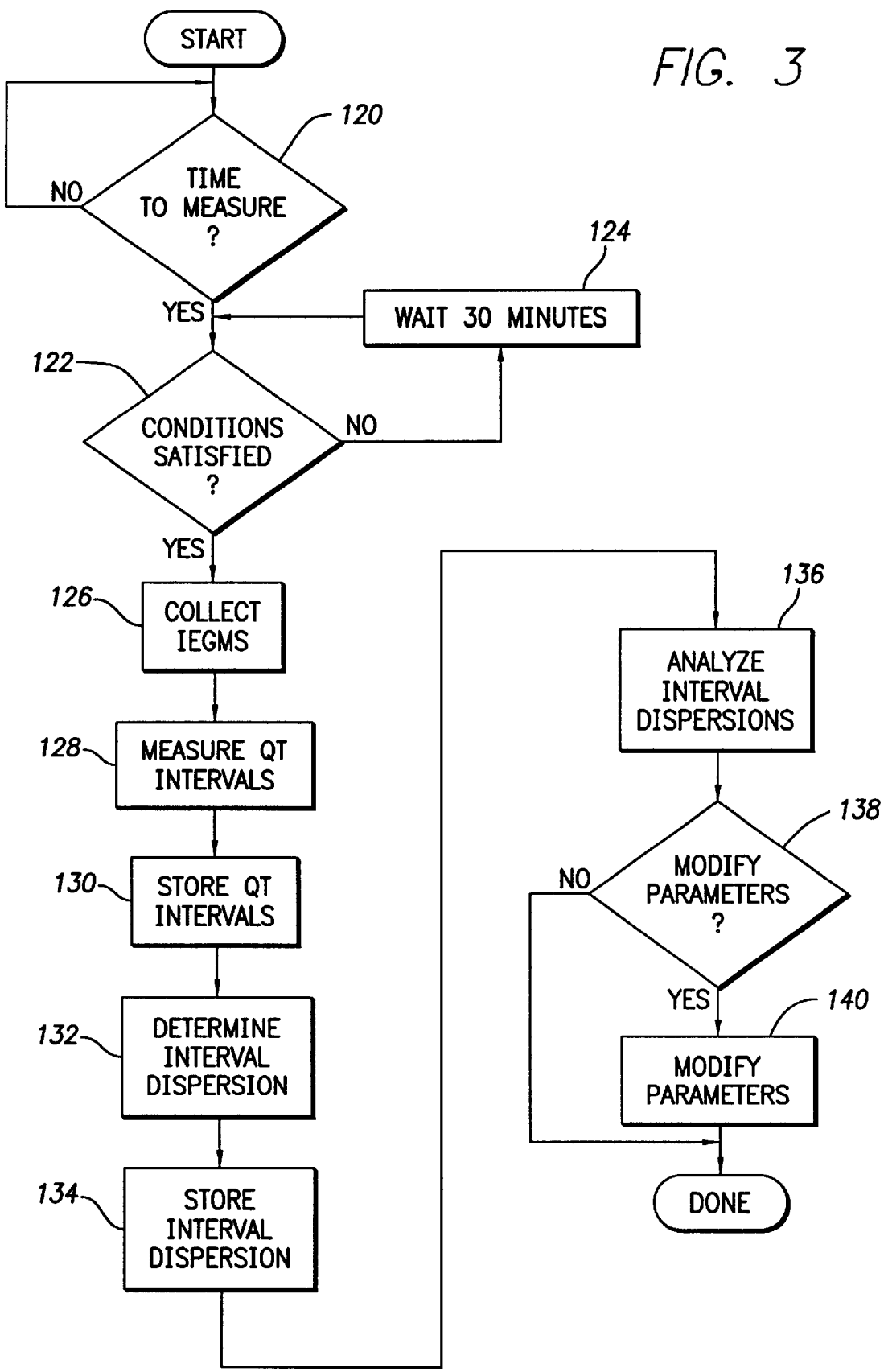
FIG. 3 is a flow chart describing an overview of the operation of one embodiment of the present invention.

In FIG. 3, a flow chart is shown describing an overview of the operation and novel features implemented in one embodiment of the present invention. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Referring now to FIG. 3, the process there illustrated initiates with decision block 120 where it is determined if it is time to measure a ventricular repolarization interval dispersion. In accordance with this preferred embodiment, the ventricular repolarization interval measured for each sensing electrode configuration is the QT interval. The QT interval dispersion, in accordance with this preferred embodiment, may be measured periodically or at preprogrammed spaced apart times. If it is time to measure the QT interval dispersion, the process advances to decision block 122. Here, the microcontroller 60 determines if preconditions are satisfied permitting the QT interval dispersions to be measured. As previously mentioned, preconditions to the measurement may be, for example, the heart rate or activity level of the patient being below predetermined limits. If the preconditions are not satisfied, the process advances to activity block 124 where the microcontroller 60 waits for a predetermined period, e.g., 30 minutes, before reinitiating decision block 122. If the preconditions are met for determining the QT interval dispersion, the process then advances to activity block 126 where the IEGMs are collected. Hence, for each sensing electrode configuration, the acquisition system 90 will provide and store in memory 94 a digitized signal representing electrical activity of the heart as sensed between each of the sensing electrode configurations.

After the heart activity signals are collected in accordance with activity block 126, the process advances to activity block 128 where the microcontroller 60 measures the QT interval in each acquired IEGM signal. Methods for determining QT intervals are well known in the art.

After the QT intervals are determined in accordance with activity block 128, the process advances to activity block 130 where the measured QT intervals are stored in memory 94. Once the QT intervals are stored in memory 94, the microcontroller 60 determines the QT interval dispersion in activity block 132. In performing activity block 132, the microcontroller 60 determines the difference between the maximum measured QT interval and the minimum measured QT interval and proceeds to activity block 134 to store the QT interval dispersion. The QT interval dispersion just determined is now available with previously determined QT interval dispersions for transmission to an external receiver for analysis.

After the QT interval dispersion is determined, the process advances to activity block 136 where the stored QT interval dispersions are analyzed. In performing activity block 136, the microcontroller 60 may, for example, determine the trend in the QT interval dispersions. Once the QT interval dispersions are analyzed, the process then advances to decision block 138 where it is determined if the trend in the QT interval dispersions merit adjustment of the pacing parameters. If adjustment is not merited, the process immediately returns. However, if the trend in the QT interval dispersions merit modification of the pacing parameters, the process then advances to activity block 140 where the pacing parameters of the device are modified. In performing activity block 140, if, for example, the QT interval dispersions are increasing, indicating that the patient may become more prone to arrhythmia or ventricular fibrillation, the device may modify the interventricular delay to change the activation sequence such that the interval dispersions are reduced. If, however, the QT interval dispersions indicate a decreasing trend, the microcontroller 60 may reduce the pacing rate or lengthen the AV interval to allow increased intrinsic activity of the patients heart with less pacemaker intervention. Once the pacing parameters are modified in accordance with activity block 140, the process returns.

As previously mentioned, along with the QT interval dispersions, the individual QT intervals, the IEGM signals, the activity level, and/or the heart rate of the patient may be stored in memory for transmission along with the QT interval dispersions for analysis. This allows the physician to accurately compare QT interval dispersions during analysis.

Figure 4:
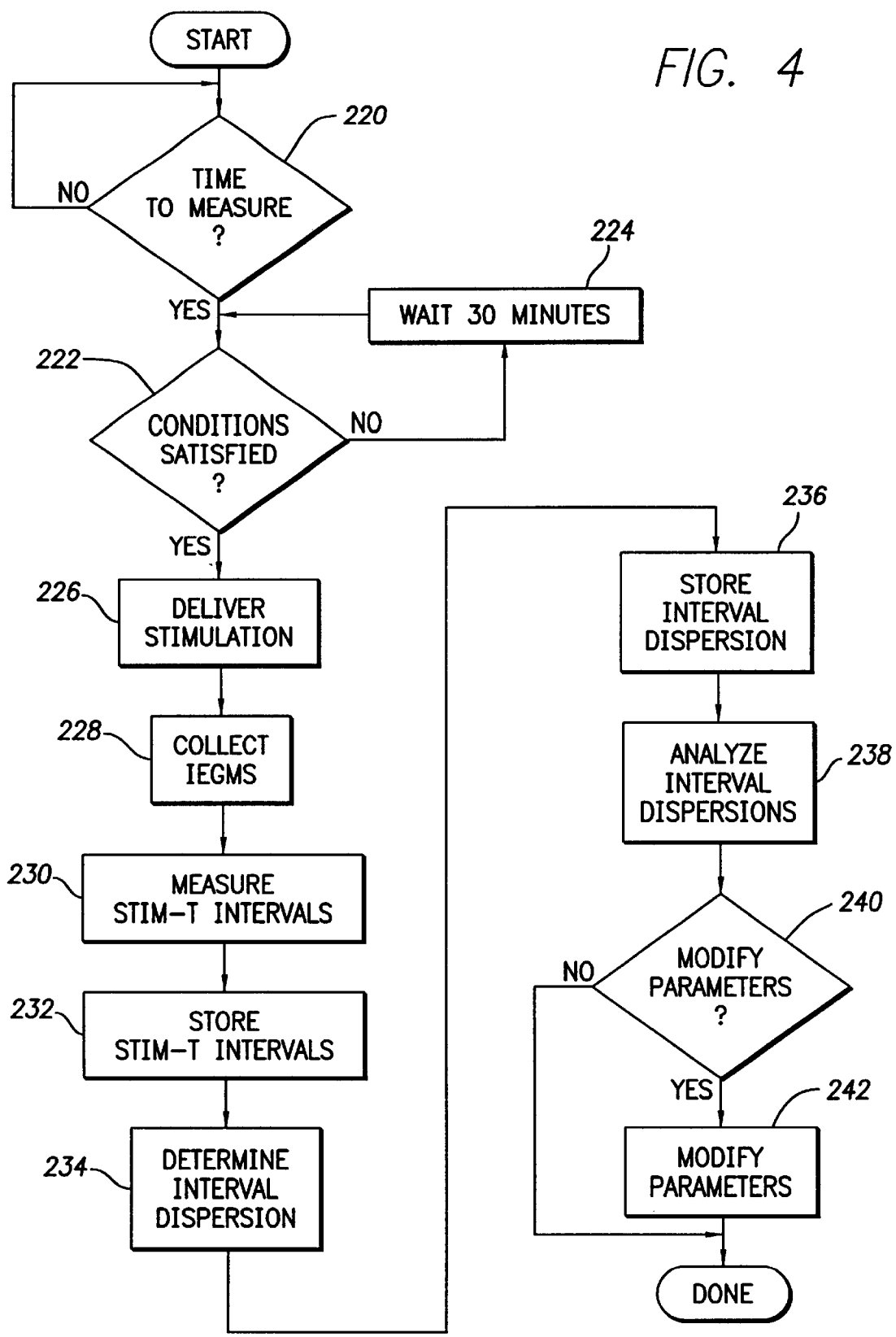
FIG. 4 is a flow chart describing an overview of the operation of another embodiment of the present invention.

Referring now to FIG. 4, a flow chart is shown which describes an overview of the operation and novel features implemented in accordance with another embodiment of the present invention. Here, the ventricular repolarization intervals which are measured are Stim-T intervals beginning with the delivery of a pacing stimulation pulse and ending at the end of the next succeeding T-wave. The delivery of the pacing stimulation pulse may be either single chamber or multi-chamber. If multi-chamber pacing is utilized, the Stim-T interval is preferably measured starting with the delivery of the pacing stimulus to the left ventricle.

The process of FIG. 4 initiates with decision block 220. In decision block 220, it is determined if it is time to measure the Stim-T interval dispersion. If it is time to measure the Stim-T interval dispersion, the process advances to decision block 222 where it is determined if the preconditions to making the measurement are satisfied. Here again, the preconditions may be, for example, the heart rate and/or the activity level of the patient being below predetermined limits. If the preconditions are not satisfied, the process then advances to activity block 224 where the process waits for 30 minutes. After 30 minutes, decision block 222 is once again initiated.

When the preconditions to making the Stim-T interval dispersion measurement are satisfied, the process then advances to activity block 226 where the pacing pulse is delivered. As previously mentioned, the pacing stimulation pulse may be single chamber, administered to the right ventricle, or multi-chamber, administered to both the right ventricle and left ventricle either simultaneously or delayed. Once the pacing stimulus has been delivered, the process advances to activity block 228 where an IEGM signal is acquired for each of the plurality of sensing electrode configurations. After the IEGMs have been collected, the process advances to activity block 230 where the Stim-T interval is measured for each IEGM signal. After the Stim-T intervals are measured, they are stored in memory 94 in accordance with activity block 232. Once stored, the Stim-T interval measurements are utilized to determine the Stim-T interval dispersion in activity block 234. In implementing activity block 234, the Stim-T interval dispersion is determined by subtracting the maximum measured Stim-T interval from the minimum measured Stim-T interval. After the Stim-T interval dispersion has been determined, the process advances to activity block 236 where the measurement is stored in memory. The Stim-T interval dispersion measurement determined in activity block 234 is now available in memory for transmission to an external receiver for analysis.

After the Stim-T interval dispersion is stored in memory, the process then advances to activity block 238 where the stored Stim-T interval dispersions are analyzed. In implementing activity block 238, the trend in the interval dispersions may be determined. Once the Stim-T interval dispersions are analyzed, the process advances to decision block 240 where it is determined if the pacing parameters of the implantable cardiac stimulation device should be modified. If the trend in the Stim-T interval dispersion measurements does not indicate modification of the pacing parameters, the process returns.

However, if modification of the pacing parameters is indicated in accordance with decision block 240, the process advances to activity block 242 where the pacing parameters are modified. Again, if the interval dispersions are increasing, the interventricular delay may be modified. If, however, the trend is a decreasing trend in the Stim-T interval dispersions, the AV delay may be increased or the pacing rate decreased to allow more intrinsic activity of the patient's heart with less pacemaker intervention.

Again, as previously described, in addition to the Stim-T interval dispersions, the individual Stim-T intervals, the IEGM signals, the current date and time, and the patient's heart rate and/or activity level may also be stored for transmission to an external receiver for analysis. This additional data may be used to present a more comprehensive picture of the patient's heart condition and support more accurate data trending.

In accordance with the present invention, long term monitoring of a patient's heart condition may be obtained by noting relative changes in ventricular repolarization interval dispersion. The ventricular repolarization intervals may be QT intervals or Stim-T intervals. The foregoing may be accomplished within an implantable cardiac stimulation device without the need for a cumbersome 12-lead ECG. The long term and periodic monitoring of QT or Stim-T interval dispersion renders assistance to the physician in assessing arrhythmic risk and titration of drug therapy. In addition, the implantable cardiac stimulation device may automatically alter pacing therapy depending upon the determined patient's risk of arrhythmia.

While the invention has been described by means of specific embodiments and applications thereof, it is understood that numerous modifications and variations could be made thereto by those skilled in the art without departing from the spirit and scope of the invention. It is therefore to be understood that within the scope of the claims the invention may be practiced otherwise than as specifically described herein.

What is claimed is:

1. In an implantable cardiac stimulation device, a system that monitors progression or regression of a patient's heart condition, the system comprising:
   a plurality of electrodes that provide a plurality of electrode configurations including right and left heart sensing electrode configurations;
   at least one sensing circuit that senses cardiac activity with the plurality of the electrode configurations to provide a plurality of electrical signals representing electrical activity of the heart;
   a processor coupled to the at least one sensing circuit and programmed to determine, at spaced apart times, a ventricular repolarization interval in each of the electrical signals and a corresponding ventricular repolarization interval dispersion;
   a memory that stores the ventricular repolarization interval dispersions over time, relative changes in the ventricular repolarization interval dispersions, over time, being indicative of the progression or regression of the patient's heart condition; and
   a telemetry circuit configured for transmitting the ventricular repolarization interval dispersions stored in the memory to an external receiver.

2. The system of claim 1 wherein the ventricular repolarization interval is a QT interval.

3. The system of claim 1 wherein the corresponding ventricular repolarization interval dispersion is the difference between a maximum ventricular repolarization interval and a minimum ventricular repolarization interval.

4. The system of claim 1 wherein the processor is configured to periodically determine the ventricular repolarization intervals.

5. The system of claim 1 wherein the implantable cardiac stimulation device includes a physiologic sensor and wherein the processor is configured to determine the ventricular repolarization intervals when the patient is at rest.

6. The system of claim 5 wherein the physiologic sensor is an activity sensor.

7. The system of claim 1 wherein the processor is configured to determine the patient's heart rate and wherein the processor is further configured to determine the ventricular repolarization intervals when the patient's heart rate is below a given heart rate.

8. The system of claim 1 wherein the processor is further configured to determine the ventricular repolarization intervals at times when the patient is normally at rest.

9. The system of claim 1 wherein the implantable cardiac stimulation device includes an activity sensor and wherein the processor is further configured to determine, at each of the spaced apart times, the patient's heart rate, the patient's activity level, the current date and the current time.

10. The system of claim 1 wherein the processor is further configured to store in the memory, along with the corresponding ventricular repolarization interval dispersion, the determined ventricular repolarization intervals, the patient's heart rate, the patient's activity level, the current date, and the current time for transmission to the external receiver along with the corresponding ventricular repolarization interval dispersion.

11. The system of claim 1 further including a pulse generator is configured to deliver a stimulation pulse to a ventricle of the heart and wherein the ventricular repolarization interval is an interval beginning with the deliverance of the stimulation pulse and ending after a T-wave.

12. The system of claim 11 wherein the pulse generator is configured to deliver bi-ventricular stimulation pulses to the right ventricle and the left ventricle and wherein the processor is configured to determine the ventricular repolarization interval beginning with the deliverance of the stimulation pulse to the left ventricle.

13. The system of claim 1 wherein the implantable cardiac stimulation device includes a pulse generator is configured to deliver pacing pulses to the heart in accordance with configured pacing parameters, and wherein the processor is configured to revise the pacing parameters in response to the relative changes in the ventricular repolarization interval dispersions.

14. In an Implantable cardiac stimulation device, a system for monitoring progression or regression of a patient's heart condition, the system comprising:
   sensing means for sensing electrical activity of the heart for providing a plurality of electrical signals representing right and left heart electrical activity;
   control means, responsive to the sensing means, for measuring, at spaced apart times, a ventricular repolarization interval in each of the electrical signals;
   means responsive to the measured ventricular repolarization intervals for determining a ventricular repolarization interval dispersion;
   storage means for storing the ventricular repolarization interval dispersions, wherein relative changes in the ventricular repolarization interval dispersions, over time, are indicative of the progression or regression in the patient's heart condition; and
   means for conveying the stored ventricular repolarization interval dispersions to a nonimplanted receiver for analysis.

15. The system of claim 14 wherein the ventricular repolarization interval is a QT interval.

16. The system of claim 14 wherein the corresponding ventricular repolarization interval dispersion is the difference between a maximum measured ventricular repolarization interval and a minimum measured ventricular repolarization interval.

17. The system of claim 14 wherein the control means includes means for periodically measuring the ventricular repolarization intervals.

18. The system of claim 14 wherein the implantable cardiac stimulation device includes physiologic sensing means for sensing patient activity and wherein the control means is responsive to the physiologic sensing means for measuring the ventricular repolarization intervals when the patient is at rest.

19. The system of claim 14 wherein the control means includes means for determining the patient's heart rate and wherein the control means measures the ventricular repolarization intervals only when the patient's heart rate is below a given heart rate.

20. The system of claim 14 wherein the control means measures the ventricular repolarization intervals only at times when the patient is normally at rest.

21. The system of claim 14 wherein the implantable cardiac stimulation device includes activity sensing means for sensing activity of the patient and wherein the control means further includes means for determining, at each of the spaced apart times, the patient's heart rate, the patient's activity level, the current date and the current time.

22. The system of claim 21 wherein the storage means further stores, along with the corresponding ventricular repolarization interval the measured ventricular repolarization intervals, the patient's heart rate, the patient's activity level, the current date, and the current time for conveyance to the external receiver along with the corresponding ventricular repolarization interval dispersion.

23. The system of claim 14 further including pacing means for delivering a pacing pulse to a ventricle of the heart and wherein the ventricular repolarization interval is an interval beginning with the deliverance of the pacing pulse and ending after a T-wave.

24. The system of claim 23 wherein the pacing means includes means for delivering bi-ventricular pacing pulses to the right ventricle and the left ventricle and wherein the control means measures the ventricular repolarization interval beginning with the deliverance of the pacing pulse to the left ventricle.

25. The system of claim 14 wherein the implantable cardiac device includes pacing means for delivering pacing pulses to the heart in accordance with configured pacing parameters and wherein the system further includes means for revising the pacing parameters in response to the relative changes in the ventricular repolarization interval dispersions.

26. In an implantable cardiac stimulation device, a method of monitoring progression or regression of a patient's heart condition, the method including the steps of:
sensing electrical activity of the heart between a plurality of different locations of the heart to provide a number of electrical signals representing right and left heart electrical activity;
deriving, at spaced apart times, a ventricular repolarization interval from each of the electrical signals;
determining, from the derived ventricular repolarization intervals, a ventricular repolarization interval dispersion; and
storing the ventricular repolarization interval dispersions in a memory, wherein relative changes in the ventricular repolarization interval dispersions, over time, are indicative of the progression or regression in the patient's heart condition.

27. The method of claim 26 wherein the step of deriving a ventricular repolarization interval includes the step of deriving a QT interval.

28. The method of claim 26 wherein the step of determining a ventricular repolarization interval dispersion includes determining the difference between a maximum ventricular repolarization interval and a minimum ventricular repolarization interval.

29. The method of claim 26 including the step of periodically deriving the ventricular repolarization intervals.

30. The method of claim 26 including the further step of sensing activity of the patient and wherein the step of deriving the ventricular repolarization intervals is performed when the patient is at rest.

31. The method of claim 26 including the further step of determining the patient's heart rate and wherein the step of deriving a ventricular repolarization interval is only performed when the patient's heart rate is below a given heart rate.

32. The method of claim 26 including the step of only deriving a ventricular repolarization interval when the patient is at rest.

33. The method of claim 26 including the further step of determining, at each of the spaced apart times, the patient's heart rate, the patient's activity level, the current date and the current time.

34. The method of claim 33 including the further step of storing, along with the ventricular repolarization interval dispersion, the derived ventricular repolarization intervals, the patient's heart rate, the patient's activity level, the current date, and the current time for conveyance to the external receiver along with the ventricular repolarization interval dispersion.

35. The method of claim 26 further including the step of delivering a pacing pulse to a ventricle of the heart and wherein the ventricular repolarization interval is an interval beginning with the deliverance of the pacing pulse and ending after a T-wave.

36. The system of claim 35 wherein the pacing step includes delivering bi-ventricular pacing pulses to the right ventricle and the left ventricle and wherein the ventricular repolarization interval is an interval beginning with the deliverance of the pacing pulse to the left ventricle.

37. The method of claim 26 wherein the implantable cardiac stimulation device applies pacing pulses to the heart in accordance with configured pacing parameters and wherein the method further includes the step of revising the pacing parameters responsive to the relative changes in the ventricular repolarization interval dispersions.

38. The method of claim 26 additionally comprising the step of conveying the stored ventricular repolarization interval dispersions to a nonimplanted receiver for analysis.

39. The method of claim 26 additionally comprising the step of conveying the stored ventricular repolarization interval dispersions to an external display suitable for trend analysis.

* * * * *